(12) United States Patent
Gupta et al.

(10) Patent No.: US 7,476,692 B2
(45) Date of Patent: Jan. 13, 2009

(54) PHARMACEUTICAL COMPOSITIONS OF SAFINGOL AND METHODS OF USING THE SAME

(75) Inventors: Shanker Gupta, Rockville, MD (US); C. Patrick Reynolds, Sherman Oaks, CA (US); Barry J. Maurer, Sylmar, CA (US); B. Rao Vishnuvajjala, Rockville, MD (US)

(73) Assignee: Childrens Hospital Los Angeles, Los Angeles, CA (US)

( * ) Notice: Subject to any disclaimer, the term of this patent is extended or adjusted under 35 U.S.C. 154(b) by 782 days.

(21) Appl. No.: 10/782,459

(22) Filed: Feb. 19, 2004

(65) Prior Publication Data

US 2005/0187186 A1 Aug. 25, 2005

Related U.S. Application Data

(60) Provisional application No. 60/449,536, filed on Feb. 21, 2003.

(51) Int. Cl.
*A61K 31/19* (2006.01)
*A61K 31/13* (2006.01)

(52) U.S. Cl. .................................. 514/557; 514/667

(58) Field of Classification Search .................. None
See application file for complete search history.

(56) References Cited

U.S. PATENT DOCUMENTS

| | | | |
|---|---|---|---|
| 5,616,332 A * | 4/1997 | Herstein | 424/401 |
| 5,677,341 A | 10/1997 | Lyons | |
| 6,368,831 B1 | 4/2002 | Maurer et al. | |
| 2002/0107265 A1 * | 8/2002 | Chen et al. | 514/310 |
| 2003/0064936 A1 * | 4/2003 | Nieuwenhuizen et al. | 514/23 |
| 2005/0181999 A1 * | 8/2005 | Ferrandis et al. | 514/28 |

FOREIGN PATENT DOCUMENTS

| EP | 1 462 081 A1 | 9/2004 |
|---|---|---|
| JP | 2000191496 A | 7/2000 |

OTHER PUBLICATIONS

Cecil's Textbook of Medicine, 21st edition, vol. 1, published in 2000, pp. 1060-1074.*
Rajewski et al., "Stereo-specific analysis of a novel protein kinase C inhibitor," Journal of Pharmaceutical and Biomedical Analysis, vol. 13, No. 3, 1995, pp. 247-253.
Database WPI, Section Ch, Week 200377, Derwent Publications Ltd., London, GB, XP-002303176, Jun. 19, 2003, 1 page.
Yamazaki et al., "Cosmetics containing stabilized sphingosines," Database accession No. 13:94300, XP002303243, Jul. 11, 2000, 1 page.
Notification of Transmittal of the International Search Report and The Written Opinion of the International Searching Authority, PCT/US2004/004960, Dec. 9, 2004.

* cited by examiner

*Primary Examiner*—Raymond J Henley, III
(74) *Attorney, Agent, or Firm*—Myers Bigel Sibley & Sajovec, PA

(57) ABSTRACT

The present invention provides stable aqueous solutions consisting essentially of: (a) a sphingolipid; (b) lactic acid; and (c) optionally a stabilizing agent; wherein the solution has a molar ratio of lactic acid to sphingolipid of 1:1 to 10:1. The present invention further provides an emulsion formulation consisting essentially of: (a) lactic acid; (b) a sphingolipid, wherein the sphingolipid is present in an amount of about 0.1 to about 30 mg/ml of emulsion; (b) optionally an isotonic agent; and (c) a phospholipid present in an amount of about 0.2 to about 200 mg/ml of emulsion. Methods of making and using the compositions are also provided.

27 Claims, No Drawings

PHARMACEUTICAL COMPOSITIONS OF SAFINGOL AND METHODS OF USING THE SAME

RELATED APPLICATIONS

The present application claims the benefit of U.S. Provisional Application Ser. No. 60/449,536, filed Feb. 21, 2003, the disclosure of which is incorporated by reference herein in its entirety.

STATEMENT OF GOVERNMENT SUPPORT

Aspects of this invention were made with the support of federal grant number CA081403 awarded by the National Institutes of Health (National Cancer Institute). The United States Government has certain rights in the invention.

FIELD OF THE INVENTION

The present invention concerns pharmaceutical compositions for delivery of sphingolipids and methods of treatment employing pharmaceutical compositions of sphingolipids.

BACKGROUND OF THE INVENTION

Safingol [L(−)-threo-dihydrosphinganine; (2S,3S)-2-amino-1,3-octadecanediol] is a synthetic optical isomer (enantiomer) of the naturally occurring sphingolipid, sphinganine (D(+)-erythro-dihydrosphinganine; (2S,3R)-2-amino-1,3-octadecanediol), and has the structure:

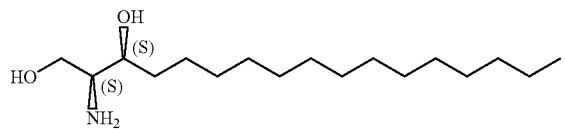

Safingol (L-threo-dihydrosphinganine)

Due to its stereochemistry, safingol has variant metabolism compared to native sphinganine both in vitro and in vivo (Stoffel, W and Bister, K., (1973) "Stereospecificities in the Metabolic Reactions of the four Isomeric Sphinganines (Dihydrosphinganines) in Rat Liver." Hopper-Seyler's Z. Physiol. Chem. 354:S169-181; Maurer, B. M., et al., (2000) "Synergistic Cytotoxicity in Solid Tumor Cell Lines Between N-(4-hydroxyphenyl)retinamide and Modulators of Ceramide Metabolism." J. Natl. Cancer Inst. 92:1897-1909; Venkatarman, K. and Futerman, A. H., (2001) "Comparison of the metabolism of L-erythro- and L-threo-sphinganines and ceramides in cultured cells and in subcellular fractions." Biochim Biophys Acta 1530:219-226.). Safingol has been variously reported to be an inhibitor of sphingosine kinase, and the various enzymes of the class, protein kinase C (PKC), including the atypical PKC subclass, PKCζ (PKCzeta), acting at the regulatory subunit of PKCs (Merrill, A. H., Jr., et al., (1986) "Inhibition of phorbol ester-dependent differentiation of human promyelocytic leukemic (HL-60) cells by sphinganine and other long-chain bases." J. Biol. Chem. 261:12610-12615; Hannun, Y. A., et al., (1986) "Sphingosine inhibition of protein kinase C activity and of phorbol dibutyrate binding in vitro and in human platelets." J. Biol. Chem. 261:12604-12609). Laboratory investigations suggest that safingol might be effective in the treatment of a variety of solid and hematopoetic cancers as a single agent, or in combination with other anticancer agents (Adams, L. M. et al., (1993) "Effect of the protein kinase C (PKC) inhibitor SPC-100270 on drug accumulation and cytotoxicity in drug resistant and sensitive tumor cells in vitro." Proc. Am. Assoc. Cancer Res. 34:410; Adams, L. M., et al., (1993) "Combined effect of the chemopotentiator SPC-100270, a protein kinase C (PKC) inhibitor, and doxorubicin (DOX) or cisplatin (CIS) on murine isografts and human tumor xenografts." Proc. Am. Assoc. Cancer Res. 34:410; Seimann, D. W., et al. (1993) "Threo-dihydrosphingosine potentiates the in vivo antitumor efficacy of cisplatin and adriamycin." Proc. Am. Assoc. Cancer Res. 34:411; Schwartz, G. K., et al. (1995) "Potentiation of apoptosis by treatment with the protein kinase C specific inhibitor safingol in mitomycin-C treated gastric cancer cells." J. Natl. Cancer Inst. 8:1394-1399; Maurer, B. M. et al., (2000), "Synergistic Cytotoxicity in Solid Tumor Cell Lines Between N-(4-hydroxyphenyl)retinamide and Modulators of Ceramide Metabolism" J. Natl. Cancer Inst. 92:1897-1909; Amin, H. M. et al., (2000) "Characterization of apoptosis induced by protein kinase C Inhibitors and its modulation by the caspase pathway in acute promyelocytic leukaemia." Br. J. Haematol 110:552-562.) A method of inhibiting oxidative burst in neutrophils using safingol as a protein kinase C inhibitors has been described in U.S. Pat. No. 4,816,450 to Bell et al. A certain method of screening to identify chemotherapeutic agents that may have increased anticancer activity when combined with safingol has been described in U.S. Pat. No. 5,821,072 to Schwartz et al. A method of treating cancer consisting of using safingol as a protein kinase C Inhibitor, in combination with other chemotherapeutic agents, has been described in U.S. Pat. No. 6,444,638 to Schwartz, et al. One hindrance to the clinical development of safingol as an anticancer agent, or anticancer potentiating agent, has been its limited aqueous solubility. Safingol can be prepared in lactic acid-containing solution, however, a simple lactic acid solution of safingol causes thrombophlebitis and hemolysis of red cells when given through peripheral veins in animals, although administration via central venous catheter reduced this toxicity (Kedderis, L. B. et al., (1995) "Toxicity of the Protein Kinase C Inhibitor Safingol Administered Alone and in Combination with Chemotherapeutic Agents." Fund. Appl. Toxicol. 25:201-217). Further, simple lactate acid solutions of safingol are unstable and prone to precipitation. An oil-in-water emulsion formulation of safingol has been described in U.S. Pat. Nos. 5,677,341 and 5,635,536 to Lyons. The emulsion of Lyons suffers from the disadvantage of being high in vegetable oil (5 to 30 g/100 ml). The emulsion formulation of Lyons received an abbreviated Phase I clinical trial in cancer patients, which was terminated prematurely for lack of drug, and is not currently in manufacture. See (Schwartz, G. K., et al., (1997) "A Pilot Clinical/Phamacological Study of the Protein Kinase C-specific Inhibitor Safingol Alone and in Combination with Doxorubicin." Clin. Cancer Res. 3:537-543. Thus, there is a need for alternative formulations of safingol for intravenous delivery and which might also be used in the treatment of disease states, including cancer.

SUMMARY OF THE INVENTION

We report herein, among other things, improved lactic acid solutions of safingol with increased stability and which can be lyophilized for storage. Further, we report herein an alternative method of preparing safingol emulsion compositions using phospholipids. Interestingly, in referring to a vegetable oil-in-water emulsion preparation of safingol, U.S. Pat. No. 5,635,536 to Lyons explicitly states that "attempts by the inventor . . . to incorporate sphingolipids into conventional soybean oil emulsions, stabilized by mixed phospholipids purified from egg yolk, were unsuccessful . . . [the] applicant tried unsuccessfully many times to produce a phospholipid-stabilized fat emulsion containing a sphingolipid." U.S. Pat. No. 6,228,399 to Parikh et al. describes the use of phospholipids in combination with at least one non-ionic, anionic, or cationic surfactants in the preparation of microparticles of water-insoluble substances. U.S. Pat. No. 5,922,355 to Parikh et al. describes the use of phospholipids in combination with at least one non-ionic, anionic, or cationic surfactant, and the additional input of energy, in the preparation of microparticles of water-insoluble substances. However, in contrast to the reports of Lyons and Parikh, we describe herein methods for the preparation of phospholipid-based emulsions of sphingolipids, in particular safingol, useful for intravenous delivery, wherein additional oils, or non-ionic, anionic, or cationic surfactants, are not necessary to achieve the stable emulsion. The present invention thus provides for, among other things, utilization of constituents preferred for clinical use over previous safingol formulations, simplicity of manufacture, decreased cost of manufacture due to reduced constituents and/or reduced complexity of manufacture.

The present invention provides novel pharmaceutical compositions of L-threo-dihydrosphingosine or "safingol." These novel pharmaceutical compositions of safingol are useful for the treatment of cancer and other hyperproliferative disorders.

In one embodiment, the present invention provides stable aqueous solutions comprising, consisting essentially of or consisting of: (a) a sphingolipid; (b) lactic acid; and (c) optionally a stabilizing agent; the solution having a molar ratio of lactic acid to sphingolipid of 1:1 to 10:1.

In other embodiments, the present invention provides reconstitutible compositions produced by the process of lyophilizing a stable aqueous solution comprising, consisting essentially of or consisting of: (a) a sphingolipid; (b) lactic acid; and (c) optionally a stabilizing agent; the solution having a molar ratio of lactic acid to sphingolipid of 1:1 to 10:1.

In still other embodiments, the present invention provides solutions, and reconstitutible compositions produced by the process of lyophilizing a stable aqueous solution, comprising, consisting essentially of, or consisting of, safingol stabilized in lactic acid, wherein a molar ratio of lactic acid to L-threo-dihydrosphingosine or safingol is about 3.5:1 to about 4:1, safingol is present in an amount of about 2.5 to about 5.0 mg/ml, the solution further comprising ethanol in an amount of about 20 mg/ml or mannitol in an amount of about 5 mg/ml.

In further embodiments, the present invention provides methods of making a stabilized solution of a sphingolipid in lactic acid, comprising, consisting essentially of or consisting of: (a) dissolving the sphingolipid in a dilute lactic acid solution, wherein the sphingolipid is present in an amount of about 0.1 to about 30 mg/ml of solution; (b) adding a stabilizing agent to the product resulting from (a); and (c) optionally lyophilizing the product resulting from (c).

Further embodiments of the present invention provide emulsion formulations comprising, consisting essentially of or consisting of: (a) lactic acid; (b) a sphingolipid, wherein the sphingolipid is present in an amount of about 0.1 to about 30 mg/ml of solution; (c) optionally an isotonic agent; and (d) a phospholipid present in an amount of about 0.2 to about 200 mg/ml of emulsion.

In other embodiments, the present invention provides methods of making an emulsion comprising, consisting essentially of or consisting of sphingolipid stabilized in an aqueous medium, comprising, consisting essentially of or consisting of: (a) dissolving the sphingolipid in a dilute lactic acid solution, wherein the sphingolipid is present in an amount of about 0.1 to about 30 mg/ml of solution; (b) optionally adding an isotonic agent; and (c) adding a phospholipid to the product resulting from (a) or (b) to thereby form said emulsion.

In still other embodiments, the present invention provides methods of treating cancer in a subject in need thereof, comprising, consisting essentially of or consisting of administering the foregoing novel compositions.

Embodiments of the present invention further provide uses of the foregoing compositions for the preparation of a medicament for carrying out the aforementioned treatments.

The foregoing and other objects and aspects of the present invention are explained in greater detail in the drawings herein and the specification set forth above.

DETAILED DESCRIPTION OF EMBODIMENTS OF THE PRESENT INVENTION

The foregoing and other aspects of the present invention will now be described in more detail with respect to embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise.

All publications, patent applications, patents and other references cited herein are incorporated by reference in their entireties.

1. Active Agents

While the present invention is initially concerned with the delivery of safingol, a variety of different active agents can be used in carrying out the present invention. Examples of active agents that can be incorporated into the compositions and formulations of the present invention include, but are not limited to, sphingolipids such as sphingosine, dihydrosphingosine, D-threo-dihydrosphingosine, L-threo-dihydrosphingosine or (2S,3S)-2-amino-1,3-octadecanediol or "safingol," DL-threo-dihydrosphingosine and lysosphingolipids. Sphingolipids are a class of lipids typically found in membranes and possess a polar head and two nonpolar tails. Sphingolipids are derived ultimately from palmitoyl-CoA and serine. They are composed of one molecule of the long-chain amino alcohol sphingosine (4-sphingenine) or one of its derivatives, optionally one molecule of a long-chain acid, a polar head alcohol and optionally phosphoric acid in the diester linkage at the polar head group. Ceramides are sphingolipids containing two acyl-moieties. The more complex, carbohydrate-containing sphingolipids, such as the cerebrosides and the gangliosides, are derived from the ceramides. Sphingolipids containing a carbohydrate are referred to as glycosphingolipids. See Lehninger et al., Principles of Biochemistry, 3rd ed. (2000).

Specific sphingolipids, such as dihydrosphingosine and the isomers D, L, or DL-threo-dihydrosphingosine, have been reported to be inhibitors of protein kinase C (PKC). See U.S. Pat. No. 6,368,831 to Maurer et al. Additionally, as noted above, safingol has been reported to be an inhibitor of sphingosine kinase. It is not excluded that safingol and other sphingolipids perform a function(s) contributory to the function of the present invention that is distinct from PKC or sphingosine kinase inhibition. Therefore, safingol, and other compounds which perform this function(s), can be active agents in the present invention and included herein, without binding applicants to a particular underlying theory of the invention.

The active compounds described above can be formulated for administration in accordance with known pharmacy techniques. See, e.g., Remington, *The Science And Practice of Pharmacy* (9th ed. 1995). In the manufacture of a pharmaceutical composition according to the present invention, the active compound (including the isomers and physiologically acceptable salts thereof) is typically admixed with, inter alia, an acceptable carrier. The carrier must, of course, be acceptable in the sense of being compatible with any other ingredients in the formulation and must not be deleterious to the patient. The carrier can be a solid or a liquid, or both, and is preferably formulated with the compound as a unit-dose formulation. One or more active compounds can be incorporated in the compositions of the invention, which can be prepared by any of the well-known techniques of pharmacy.

The pharmaceutical compositions according to embodiments of the present invention include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intracerebral, intraarterial, or intravenous), although the most suitable route in any given case will depend on the nature and severity of the condition being treated and on the nature of the particular active agent which is being used.

In particular embodiments, pharmaceutical compositions according the present invention are suitable for parenteral administration. Such parenteral formulations can comprise the active compound, which preparations are preferably isotonic with the blood of the intended recipient. These preparations can be administered by means of subcutaneous, intramuscular, intradermal, intrathecal injection, epidural injection, intraventricular injection into a ventricle of the brain or intravenous injection. Such preparations may conveniently be prepared by admixing the compound with an agent to render the resulting solution sterile and isotonic with the blood. In some embodiments, the pharmaceutical compositions according the present invention are administered by way of intravenous injection.

In addition to active agents or their salts, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. The pharmaceutical compositions of the present invention can be lyophilized using techniques well known in the art.

2. Solution Formulations

The pharmaceutical compositions described above may be formulated for administration in a pharmaceutical carrier in accordance with known techniques of pharmacy. See, e.g., Remington, *The Science And Practice of Pharmacy* (9th Ed. 1995).

The pharmaceutical compositions according to embodiments of the present invention include stable aqueous solutions, and stable phospholipid-containing emulsions.

The pharmaceutical compositions according to embodiments of the present invention include stable aqueous solutions comprising, consisting essentially of or consisting of: (a) a sphingolipid; (b) lactic acid; and (c) optionally a stabilizing agent; the solution having a molar ratio of lactic acid to sphingolipid of 0.5:1 or 1:1 up to 10:1 or 20:1.

The sphingolipid can be any sphingolipid as understood by one skilled in the art and as described above. In some embodiments, the sphingolipid can be sphingosine, dihydrosphingosine, D-threo-dihydrosphingosine, L-threo-dihydrosphingosine or safingol, DL-threo-dihydrosphingosine, lysosphingolipids, combinations thereof and pharmaceutically acceptable salts thereof. In particular embodiments, the sphingolipid is safingol. The sphingolipid can be included in the solution in an amount of from about 0.1 to about 30 mg/ml. In particular embodiments, the sphingolipid can be included in the solution in an amount from about 2.5 to about 5.0 mg/ml. In particular embodiments, the aqueous medium is water.

The stabilizing agent that is optionally present in the stable aqueous solution can increase the stability of the sphingolipid in the lactic acid solution. The stabilizing agent can also increase the solubility of the sphingolipid in the lactic acid solution. Hence, "stabilizing agent" and "solubilizing agent" can be used interchangeably. Additionally, the stabilizing agent can act as a bulking agent in the lyophilization process. The stabilizing agent can be an alcohol or a polyhydroxy alcohol. The alcohol or a polyhydroxy alcohol can be added in an amount of about 0.5 to about 500 mg/ml. In some embodiments, the alcohol can be ethanol. In some embodiments, the polyhydroxy alcohol can be mannitol. In particular embodiments, the solution can comprise ethanol in an amount of about 20 mg/ml. In other embodiments, the solution can comprise mannitol in an amount of about 5 mg/ml.

The solution can be lyophilized to provide, among other things, additional improved storage properties, and reconstituted for use with a suitable diluent for delivery, for example, water or water and ethanol.

In particular embodiments, the stable solutions comprise safingol stabilized in lactic acid, wherein a molar ratio of lactic acid to safingol is about 1:1 or 3.5:1 to about 4:1 or 6:1, safingol is present in an amount of about 2.5 to about 5.0 mg/ml, the solution further comprises ethanol in an amount of about 20 mg/ml or mannitol in an amount of about 5 mg/ml.

Embodiments of the present invention further provide methods of making a stabilized solution of a sphingolipid in lactic acid. Variations on the general synthetic methods will be readily apparent to those skilled in the art and are deemed to be within the scope of the present invention. In particular, methods of making a stabilized solution of a sphingolipid in lactic acid comprise, consists essentially of or consists of: (a) dissolving the sphingolipid in a dilute lactic acid solution; (b) adding a stabilizing agent to the product resulting from (a); and (c) optionally lypholizing the product resulting from (c).

The sphingolipids and amounts thereof are described above as are the stabilizing agents and amounts thereof. In some embodiments, the solution can be sterilized by filtration or other processes known to those skilled in the art. The solution can also be lyophilized as noted above.

3. Emulsion Formulations

The pharmaceutical compositions according to embodiments of the present invention also include emulsion formulations comprising, consisting essentially of or consisting of: (a) lactic acid; (b) a sphingolipid, wherein the sphingolipid is present in an amount of about 0.05 or 0.1 to about 30 or 60 mg/ml of solution; (c) optionally an isotonic agent; and (d) a phospholipid present in an amount of about 0.1 or 0.2 to about 200 or 400 mg/ml of emulsion.

The sphingolipid can be any sphingolipid as understood by one skilled in the art and as described above. In some embodiments, the sphingolipid can be sphingosine, dihydrosphingosine, D-threo-dihydrosphingosine, L-threo-dihydrosphingosine or safingol, DL-threo-dihydrosphingosine, lysosphingolipids, combinations thereof and pharmaceutically acceptable salts thereof. In particular embodiments, the sphingolipid is safingol. In some embodiments, safingol can be present in an amount of about 2.0 mg/ml of solution.

In particular embodiments, the molar ratio of lactic acid to sphingolipid is about 0.5:1 or 1 to about 10:1 or 20:1. In other embodiments, the molar ratio of lactic acid to sphingolipid is about 2:1 and the lactic acid is 1.2 mg/ml solution. In particular embodiments, the aqueous medium is water.

An isotonic agent can be added in an amount of about 1 to about 100 mg/ml. The isotonic agent can be an aldose such as glucose, or an alcohol such as glycerol, or other agent as understood by one skilled in the art. In particular embodiments, the isotonic agent is glucose. In some embodiments, glucose is present in an amount of about 45 to about 50 mg/ml.

The phospholipid can be any efficacious natural or synthetic phospholipid or combination thereof as understood by one skilled in the art. Examples of such phospholipids include, but are not limited to, phosphatidylcholine, phosphatidylethanolamine, phosphatidylserine, phosphatidylinositol, phosphatidylglycerol, phosphatidic acid, lysophospholipid, egg phospholipid, soybean phospholipid and combinations thereof. The phospholipids can be salted or desalted, hydrogenated or partially hydrogenated or natural semisynthetic or synthetic.

The phospholipid can be present in an amount of about 0.2 to about 200 mg/ml of emulsion. In particular embodiments, the phospholipid mixture is Lipoid E80® (Lipoid KG, Germany) wherein Lipoid E80® is about 80% w/w phosphatidylcholine, 8% w/w phosphatidylethanolamine, 2.5% w/w nonpolar lipids, and 3% w/w sphingomyelin. In other embodiments, the Lipoid E80® is 20 mg/ml emulsion.

Consequently, the phospholipid-based emulsions have minimal vegetable oil content. In some embodiments, the emulsions have less than about 5% or about 10% vegetable oil. In a particular embodiment, the emulsion has an absence of vegetable oils, i.e., the emulsion is essentially free of vegetable oils.

In some embodiments, the mean particle size of the emulsion is less than about 0.2 microns. In a particular embodiment, the mean particle size of the emulsion is less than about 0.03 microns.

In particular embodiments, emulsions of the present invention have a shelf-life of at least three months when stored at temperatures from about 2° C. to about 8° C. In some embodiments, the emulsions have a shelf-life of at least six months when stored at temperatures from about 2° C. to about 8° C. In other embodiments, the emulsions have a shelf-life of at least nine months when stored at temperatures from about 2° C. to about 8° C. As used herein, "shelf-life" refers to the time period in which the emulsion lasts without undergoing significant chemical or physical changes. For example, the emulsion can remain an emulsion and does not undergo a substantial change in appearance or precipitation for a specified period of time. Additionally, in some embodiments, the emulsions have an increased circulation time in the blood stream after administration in comparison to control solutions. In some embodiments, the emulsions exhibit an improved clearance from the pulmonary bed after central venous catheter administration, decreasing the concentration of free sphingolipids into the pulmonary bed, and possibly reducing pulmonary toxicity due to increased point-concentrations of free sphingolipids, particularly safingol, in the lungs.

Embodiments of the present invention further provide methods of making an emulsion formulation. Variations on the general synthetic methods will be readily apparent to those skilled in the art and are deemed to be within the scope of the present invention. In particular, methods of making an emulsion formulation comprise, consists essentially of or consists of: (a) dissolving the sphingolipid in a dilute lactic acid solution; (b) optionally adding an isotonic agent; and (c) adding a phospholipid to the product resulting from (a) or (b) to thereby form the emulsion.

The sphingolipids and amounts thereof, isotonic agents and amounts thereof and phospholipids and amounts thereof are described above. In some embodiments, phospholipids can be added to form a pre-emulsion. In other embodiments, the emulsion can be sterilized by filtration or other processes known to those skilled in the art.

4. Treatment and Administration

The pharmaceutical compositions of the present invention can be administered for the treatment of hyperproliferative disorders such as tumors, cancers, and neoplastic disorders, as well as premalignant and non-neoplastic or non-malignant hyperproliferative disorders. In some embodiments of the present invention, the pharmaceutical compositions can induce apoptosis or necrosis, or both, in cancer cells or angiogenesis in the tumor bed.

Examples of tumors, cancers, and neoplastic tissue that can be treated by the present invention include, but are not limited to, malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers; colon, esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include, but are not limited to, myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. As used herein, "treatment" is not necessarily meant to imply cure or complete abolition of hyperproliferative growths. As used herein, a "treatment effective amount" is an amount effective to result in the killing, the slowing of the rate of growth of hyperproliferative cells or tumor or cancerous growth, the decrease in size of a body of hyperproliferative cells or tumor or cancerous growth, and/or the reduction in number of hyperproliferative cells or tumor or cancerous growth. The treatment effective amount of the active agent, the use of which is in the scope of present invention, will vary somewhat from patient to patient, and will depend upon factors such as the age and condition of the patient and the route of delivery. A potentiating agent (or agents) can be included in an amount sufficient to enhance the activity of the first compound, such that the two (or more) compounds together have greater therapeutic efficacy than the individual compounds given alone (e.g., due to synergistic interaction; reduced combined toxicity, etc.).

Dosages can be determined in accordance with routine pharmacological procedures known to those skilled in the art. As a general proposition, a dosage from about 0.1 to about 50 mg/kg/day will have therapeutic efficacy, with all weights being calculated based upon the weight of the active agent. Toxicity concerns at the higher level may restrict dosage. A dosage from about 10 mg/kg to about 50 mg/kg may be employed for oral administration. Safingol can be administered intravenously to achieve peak serum levels of about 1 to 10 µM (e.g., 7.5 µM), or dosages of 1 or 5 to 20 mg/kg (e.g., 10 mg/kg). In particular embodiments, the present invention enables greater delivery of safingol to the subject with fewer side effects.

The frequency of administration is usually one, two, or three times per day as a bolus, or by continuous intravenous infusion, or as necessary to control the condition. The duration of treatment depends on the type of condition being treated and may be for as long as the life of the patient.

In particular embodiments, the active compounds can be administered in combination. As used herein, the administration of two or more compounds "in combination" means that the two compounds are administered closely enough in time that the presence of one alters the biological effects of the other. The two compounds can be administered simultaneously (concurrently) or sequentially. Simultaneous administration can be carried out by mixing the compounds prior to administration, or by administering the compounds at the same point in time but at different anatomic sites or using different routes of administration. The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The compositions described herein can be used in combination therapies, such as described in U.S. Pat. Nos. 6,368,831 and 6,352,844 to Maurer et al. the disclosures of which are incorporated by reference herein in their entirety. In one embodiment, the combination therapy is safingol and fenretinide.

Further embodiments of the present invention will now be described with reference to the following examples. It should be appreciated that these examples are for the purposes of illustrating embodiments of the present invention, and do not limit the scope of the invention.

EXAMPLE 1

Solubility and Stability of Safingol in Lactic Acid Solution

The following solubility/miscibility studies were performed with safingol at various concentrations. As shown below in Table 1, ethanol substantially increased the solubility of safingol in a lactic acid/water solutions. Additionally, it was noted that the precipitates that formed when ethanol-containing safingol/lactic acid solutions were chilled to 2-8° C. were reduced in quantity and dissolved much more readily than similar precipitates in non-ethanol-containing safingol/lactic acid solutions upon warming to room temperature, as for delivery.

TABLE 1

| Solvent/solvent system | Result |
|---|---|
| 50:50 Ethanol:WFI with lactic acid | soluble almost up to 50 mg/mL, but precipitate formation at 2° C. to 8° C. |
| 60:40 t-BuOH/WFI | soluble to 15.68 mg/mL |
| Castor oil | not soluble |
| Citric acid/WFI | not soluble |
| Diluent 12 | 7.22 mg/mL max solubility |
| DMAC | soluble between 6.6 to 7.4 mg/mL |

TABLE 1-continued

| Solvent/solvent system | Result |
|---|---|
| DMSO | not soluble |
| Ethanol | soluble between 7.5 to 8.2 mg/mL |
| HCl/Ethanol | not soluble |
| HCl/WFI | not soluble |
| Lactic acid in 2% EPL in WFI | solubility similar to lactic without EPL, but no precipitate at 2° C. to 8° C. |
| Lactic acid in WFI with 5 mg/mL mannitol | soluble to 10 mg/mL |
| Lactic acid/Ethanol | soluble almost up to 20 mg/mL, but precipitate formation at 2° C. to 8° C. |
| Lactic acid/WFI | soluble to >10 mg/mL, but precipitate formation at 2° C. to 8° C. |
| Maleic acid/WFI | not soluble |
| Malic acid/WFI | not soluble |
| Methanesulfonic acid/Ethanol | not soluble |
| Methanesulfonic acid/WFI | not soluble, but the appearance of the safingol changed, indicating possible formation of the mesylate salt. |
| Neobee oil | Not soluble (later found to be soluble only at approx. 80° C.). Note: While neobee oil did not demonstrate true solubility of safingol, the result was a hazy mixture without visible particles present. This was observed at 0.5 and 1.0 mg/mL. |
| PEG 300 | max solubility between 1.01 to 1.06 mg/mL |
| Pluronic F-68/WFI | not soluble |
| Propionic acid/WFI | Soluble at 5 mg/mL; precipitate formation at 2° C. to 8° C. |
| Propylene Glycol | max solubility between 1.06 to 1.35 mg/mL |
| Safflower oil | Not soluble (attempted: 0.5 mg/mL) |
| Sesame oil | Not soluble (attempted: 0.5 mg/mL) |
| Sodium Lactate/WFI | not soluble |
| Soybean oil | Not soluble (later found to be soluble only at approx. 80° C.) |
| Tartaric acid/WFI | not soluble |
| t-Butanol (t-BuOH) | soluble to >25 mg/mL |
| Tricaprylin | Not soluble (attempted: 0.5 mg/mL) |
| Tween-80 | not soluble |
| Valium solvent | Not soluble (attempted: 0.5 mg/mL) |
| Vitamin E (α-tocopherol) | not soluble |

EXAMPLE 2

Stability of Safingol Solution

An accelerated stability study was conducted in order to evaluate safingol drug stability in the liquid dosage form (lactic acid solution, 2% (v/v) ethanol). BVL Pilot Lot SG012902 vials (safingol 5.0 mg/mL, 6 mg/ml (4 eq) lactic acid, 2% (v/v) ethanol) and BVL Pilot Lot SG013002 vials (safingol 2.5 mg/mL, 3 mg/ml lactic acid, 2% (v/v) ethanol) were placed on stability at room temperature (25° C.±2° C./60%±5% relative humidity), and at accelerated incubation (40° C.±2° C./75%±5% relative humidity) and in a 50° C. oven. Results are summarized in Tables 2a-f below and demonstrated solution stability at 25° C. for at least three months.

TABLE 2a

Safingol Lactate Pilot Lot SG012902, 5 mg/mL
25° C. ± 2° C./60% ± 5% relative humidity

| MONTH/ STORAGE | | POTENCY (mg/mL) n = 2 | % (theoretical = 5.0 mg/mL) | pH | APPEARANCE |
|---|---|---|---|---|---|
| 0 | N/A | 4.98 | 99.6 | 3.02 | Clear and colorless solution with no visible particulates. |
| 1 | Up | 4.99 | 99.8 | 3.03 | No change, same as T = 0 |
| | Inverted | 5.04 | 100.8 | 3.03 | No change, same as T = 0 |
| 2 | Up | 5.02 | 100.4 | 3.20 | No change, same as T = 0 |
| | Inverted | 5.00 | 100.0 | 3.19 | No change, same as T = 0 |
| 3 | Up | 4.85 | 97.0 | 3.02 | No change, same as T = 0 |
| | Inverted | 4.95 | 99.0 | 2.99 | No change, same as T = 0 |

TABLE 2b

Safingol Lactate Pilot Lot SG012902, 5 mg/mL
40° C. ± 2° C./75% ± 5% relative humidity

| MONTH/ STORAGE | POTENCY (mg/mL) n = 2 | % (theoretical = 5.0 mg/ml) | pH | APPEARANCE |
|---|---|---|---|---|
| 0 N/A | 4.98 | 99.6 | 3.02 | Clear and colorless solution with no visible particulates. |
| 1 Up | 4.95 | 99.0 | 3.03 | Clear and colorless for the first 8 hours then a precipitate formed the following day. |
| Inverted | 4.95 | 99.0 | 3.04 | Clear and colorless for the first 8 hours then a precipitate formed the following day. |
| 2 Up | 4.84 | 96.8 | 3.18 | Clear and colorless for the first 8 hours then a precipitate formed the following day. |
| Inverted | 4.85 | 97.0 | 3.20 | Clear and colorless for the first 8 hours then a precipitate formed the following day. |
| 3 Up | 4.81 | 96.2 | 2.99 | Clear and colorless for the first 8 hours then a precipitate formed the following day. |
| Inverted | 4.85 | 97.0 | 2.98 | Clear and colorless for the first 8 hours then a precipitate formed the following day. |

TABLE 2c

Safingol Lactate Pilot Lot SG012902, 5 mg/mL
50° C. ± 2° C.

| MONTH/ STORAGE | POTENCY (mg/mL) n = 2 | % (theoretical = 5.0 mg/mL) | pH | APPEARANCE |
|---|---|---|---|---|
| 0 N/A | 4.98 | 99.6 | 3.02 | Clear and colorless solution with no visible particulates. |
| 1 Up | 4.91 | 98.2 | 3.05 | Clear and colorless for the first 8 hours then a precipitate formed the following day. |
| Inverted | 4.91 | 98.2 | 3.08 | Clear and colorless for the first 8 hours then a precipitate formed the following day. |
| 2 Up | 4.79 | 95.8 | 3.22 | Clear and colorless for the first 8 hours then a precipitate formed the following day. |
| Inverted | 4.80 | 96.0 | 3.18 | Clear and colorless for the first 8 hours then a precipitate formed the following day. |
| 3 Up | 4.80 | 96.0 | 2.97 | Clear and colorless for the first 8 hours then a precipitate formed the following day. |
| inverted | 4.74 | 94.8 | 2.95 | Clear and colorless for the first 8 hours then a precipitate formed the following day. |

TABLE 2d

Safingol Lactate Pilot Lot SG013002, 2.5 mg/mL
25° C. ± 2° C./60% ± 5% relative humidity

| MONTH/ STORAGE | POTENCY (mg/mL) n = 2 | % (theoretical = 2.5 mg/mL) | pH | APPEARANCE |
|---|---|---|---|---|
| 0 N/A | 2.56 | 102.4 | 2.95 | Clear and colorless solution with no visible particulates. |
| 1 Up | 2.58 | 103.2 | 2.94 | No change, same as T = 0 |
| Inverted | 2.50 | 100.0 | 2.93 | No change, same as T = 0 |
| 2 Up | 2.46 | 98.4 | 3.18 | No change, same as T = 0 |
| Inverted | 2.52 | 100.8 | 3.20 | No change, same as T = 0 |
| 3 Up | 2.47 | 98.8 | 3.08 | No change, same as T = 0 |
| Inverted | 2.44 | 97.6 | 3.06 | No change, same as T = 0 |

TABLE 2e

Safingol Lactate Pilot Lot SG013002, 2.5 mg/mL
40° C. ± 2° C./75% ± 5% relative humidity

| MONTH/STORAGE | POTENCY (mg/mL) n = 2 | % (theoretical = 2.5 mg/mL) | pH | APPEARANCE |
|---|---|---|---|---|
| 0 N/A | 2.56 | 102.4 | 2.95 | Clear and colorless solution with no visible particulates. |
| 1 Up | 2.57 | 102.8 | 2.93 | Clear and colorless solution with no visible particulates. |
| Inverted | 2.52 | 100.8 | 2.93 | Clear and colorless solution with no visible particulates. |
| 2 Up | 2.38 | 95.2 | 3.21 | Clear and colorless for the first 8 hours then a precipitate formed the following day. |
| Inverted | 2.39 | 95.6 | 3.22 | Clear and colorless for the first 8 hours then a precipitate formed the following day. |
| 3 Up | 2.39 | 95.6 | 3.08 | Clear and Colorless for the first 8 hours then a precipitated formed the following day. |
| Inverted | 2.41 | 96.4 | 3.08 | Clear and colorless for the first 8 hours then a precipitate formed the following day. |

TABLE 2f

Safingol Lactate Pilot Lot SG013002, 2.5 mg/mL
50° C. ± 2° C.

| MONTH/STORAGE | POTENCY (mg/mL) n = 2 | % (theoretical = 2.5 mg/mL) | pH | APPEARANCE |
|---|---|---|---|---|
| 0 N/A | 2.56 | 102.4 | 2.95 | Clear and colorless solution with no visible particulates. |
| 1 Up | 2.46 | 98.4 | 2.95 | Clear and colorless for the first 8 hours then a precipitate formed the following day. |
| Inverted | 2.43 | 97.2 | 2.98 | Clear and colorless for the first 8 hours then a precipitate formed the following day. |
| 2 Up | 2.35 | 94.0 | 3.23 | Clear and colorless for the first 8 hours then a precipitate formed the following day. |
| Inverted | 2.43 | 97.2 | 3.25 | Clear and colorless for the first 8 hours then a precipitate formed the following day. |
| 3 Up | 2.34 | 93.6 | 3.06 | Clear and colorless for the first 8 hours then a precipitate formed the following day. |
| inverted | 2.34 | 93.6 | 3.07 | Clear and colorless for the first 8 hours then a precipitate formed the following day. |

EXAMPLE 3

Lyophilization of Safingol Solutions and Reconstitution of Lyophilized Safingol Lyophilization (freeze-drying) of drugs can extend shelf life and permit higher storage temperatures. Solubility was tested of safingol in lactic acid/WFI/mannitol with the intention of lyophilization. Lyophilization cycles were run on formulations containing safingol at 5 and 10 mg/mL, with and without mannitol, and a t-BuOH/WFI formulation (all were brought to final volume with WFI=Water For Infusion). As shown in the Tables below in Tables 3a-e and Table 4, the addition of mannitol gives desirable properties facilitating lyophilization of safingol, and the use of ethanol-containing solutions when reconstituting the lyophilized safingol, for delivery both reduced foaming and stabilized the solution against precipitation.

TABLES 3a-e

| | Amount (mg/mL) |
|---|---|
| Pilot Lot RN102300-1 | |
| Safingol | 10 |
| Lactic Acid | 10.5 |
| | (3.5 molar equivalents) |
| Pilot Lot RN102300-2 | |
| Safingol | 10 |
| Lactic Acid | 10.5 |
| | (3.5 molar equivalents) |
| Mannitol | 5 |
| Pilot Lot RN102300-3 | |
| Safingol | 5 |
| Lactic Acid | 5.25 |
| | (3.5 molar equivalents) |
| Pilot Lot RN102300-4 | |
| Safingol | 5 |

TABLES 3a-e-continued

| | Amount (mg/mL) |
|---|---|
| Lactic Acid | 5.25 |
| | (3.5 molar equivalents) |
| Mannitol | 5 |

| Pilot Lot RN102300-T | |
|---|---|
| Safingol | 5 |
| Butanol | 50% in Water |

The lyophilization cycle for lots RN102300-1 through RN102300-T was as follows:
1. Product was loaded on a pre-chilled shelf set at 0° C.
2. Shelf was brought to −45° C. and held until all product thermocouples were below −45° C.
3. The vacuum was started using a nitrogen sweep of 104 microns to 195 microns.
4. Shelf was ramped to −35° C. and held for 43.5 hours.
5. Shelf was ramped to −15° C. and held approximately 24 hours.
6. Shelf was ramped to 25° C. and held until all product thermocouples were above 24° C.
7. Best vacuum was pulled at about 19 microns and held for approximately nine hours.
8. Chamber was brought to atmospheric conditions and vials were stoppered.

Results: Vials without mannitol exhibited an amount of melt back (structural collapse) making their reconstitution for delivery more difficult.

TABLES 4a and b

| Pilot lot RN120500-25 & -50 | | |
|---|---|---|
| | Amount (mg/mL) | |
| | RN120500-25 | RN120500-50 |
| Safingol | 5 | 10 |
| Lactic Acid | 5.25 | 10.5 |
| | (3.5 molar equivalent) | (3.5 molar equivalents) |
| Mannitol | 5 | 5 |

| Pilot lot 072401-25 & -50 | | |
|---|---|---|
| | Amount (mg/mL) | |
| | RN072401-25 | RN072401-50 |
| Safingol | 5 | 10 |
| Lactic Acid | 5.25 | 10.5 |
| | (3.5 molar equivalent) | (3.5 molar equivalents) |
| Mannitol | 5 | 5 |

The lyophilization cycle for lots RN120500-25 and -50 and RN072401-25 and -50 was as follows:
1. Product was loaded on a pre-chilled shelf set at −45° C.
2. Shelf temperature was held until all product thermocouples were below −45° C.
3. The vacuum was started using a nitrogen sweep of 100 microns to 150 microns.
4. Shelf was ramped to −35° C. and held until all thermocouples reached −35° C., which was approximately 3 days.
5. Shelf was ramped to −25° C. and held until all thermocouples reached −25° C., which was about 6.5 hours.
6. Shelf was ramped to −10° C. and held until all thermocouples reached −10° C., which was approximately 6 hours.
7. Shelf was ramped to 25° C. and held until all thermocouples reached 25° C., which was about 6.5 hours.
8. Best vacuum was pulled for 24 hours.
9. Chamber was brought to atmospheric conditions and vials were stoppered.

Results: All vials were uniform and no melt back was exhibited.

RESULTS

The lot with t-Butanol, RN102300-T, did not reconstitute but formed a cloudy white mixture upon addition of water.

The lyophilized products (lots RN102300-1 through RN102300-4, RN120500-25, RN120500-50, RN072401-25, and RN072401-50) that contained 25 mg/vial mannitol, 25 mg/vial and 50 mg/vial Safingol, and 3.5 molar equivalents of Lactic Acid reconstituted in less than one minute with shaking.

However, these lots showed considerable foaming when reconstituted with 5 mL of water. The foam was analyzed and it was discovered that the foam contained Safingol. It was also found that when the foam began to settle, a precipitate formed at the bottom of the vial.

Diluting solvents, which contained various amounts of ethanol were then evaluated for reconstituting the lyophilized product. Ethanol was used at 10% v/v and 25% v/v. During reconstitution, the 25% ethanol solution produced very little foam, which disappeared after the solution remained at room temperature for less than 20 minutes, no precipitate was noticed, and exhibited a 3-day stability after reconstitution. The vial reconstituted with 10% ethanol solution produced more foam than the vial reconstituted with 25% ethanol. No precipitate was noticed in the vial reconstituted with 10% ethanol after 24 hours.

EXAMPLE 4

Preparation of Safingol Emulsion

An exemplary method for producing a safingol emulsion is described below. Variations on the general synthetic methods will be readily apparent to those skilled in the art and are deemed to be within the scope of the present invention.

TABLE 5

| LABEL AMOUNT (g/mL) | INGREDIENT | MANUFACTURER | STORAGE |
|---|---|---|---|
| 0.002 (pure) | NSC 714503* (Safingol) | Avanti | −10° C. to −20° C. |
| 0.020 (pure) | Egg Phospholipids Lipoid E80 ®*, ** | Lipoid | −10° C. to −20° C. |
| 0.0454 | Dextrose, Anhydrous, USP | Mallinckrodt | +15° C. to +30° C. |
| 0.0012 | Lactic Acid, USP | J. T. Baker | +15° C. to +30° C. |
| QS to 1.0 mL | Water For Injection, USP/EP | Ben Venue | N/A |

*Allow to warm to room temperature for a minimum of one hour before opening, weighing

TABLE 6

COMPOUNDING PRECAUTIONS/CONDITIONS

| | |
|---|---|
| APPROX. TOTAL COMPOUNDING TIME | FOR A 100 L BATCH: COMPOUNDING (PRE-HOMOGENIZATION): 2 HOURS, EQUIPMENT SET-UP: 2 TO 4 HOURS HOMOGENIZATION PROCESS: 6 TO 10 HOURS |
| ACTIVE DRUG SUBSTANCE INFORMATION/ RESTRICTIONS | Active Drug Substance is a very light flaky material that may easily become airborne. |
| TEMPERATURE | Ambient temperature for compounding; Post compounding and homogenization 2° C. to 15° C. |
| ADS BALANCE/SCALE | ANALYTICAL |
| COMPOUNDING EQUIPMENT | 1. Compounding Vessel must be jacketed, fitted with both prop mixer and rotor/stator mixer, and sized to contain total batch. 2. Microfluidizer M210C-E/H requires two homogenization vessels, each fitted with a prop mixer. |
| MIXING RATE | Prop mixer: 800 rpm to 1,200 rpm, Rotor Stator mixer: control by mixing time. |
| LIGHTING | YELLOW LIGHTING REQUIRED |
| NITROGEN, NF PROTECTION | NITROGEN PROTECTION IS NOT REQUIRED. |
| pH SPECIFICATION | NONE REQUIRED |
| TIME CONSTRAINTS | BVL SOP |
| CONTACT MATERIAL RESTRICTIONS/ SPECIFICATIONS | NO KNOWN RESTRICTIONS |
| LOW OXYGEN WATER REQUIREMENT | NO |
| CLARIFICATION REQUIREMENT | YES; PRIOR TO HOMOGENIZATION. Gelman Polypure TDC, 1 µm |
| OTHER PRECAUTIONS (Critical Process Variables) | 1. FORMULATION REQUIRES PARTICLE SIZE MONITORING (QC). 2. FORMULATION REQUIRES COOLING TO MAINTAIN SOLUTION TEMPERATURE WITHIN +2° C. to +15° C. RANGE. |

Process Overview:

Pre-Emulsion Preparation:

For the manufacture of this emulsion product, the drug and excipients are initially combined using a rotor/stator homogenizing mixer. The pre-emulsion at this stage appears uniform but has a broad particle size distribution that requires further size reduction by homogenization to stabilize it as an emulsion and permit sterile filtration.

Homogenization:

The pre-emulsion is homogenized through the Microfluidizer to bring the particle size below filterable range (0.22 µm). Samples of the emulsion are withdrawn at predetermined passes to monitor the particle size. The particle size measurements are used to determine when homogenization is complete.

Adequate cooling is required for the Microfluidizer during homogenization; circulation of cold water is maintained through both water baths.

A. Formulation:
1. The compounding vessel should be jacketed and contain both a Silverson (rotor/stator mixer) and a prop mixer.
2. Add Water For Injection, USP/EP in an amount equivalent to 70% of the final batch QS weight. Temperature range: +15° C. to +30° C.
3. Start mixing with the prop mixer. (800 rpm to 1,200 rpm).
4. Add the Lactic Acid, USP.
5. Rinse with three (3) portions of Water for Injection, total not exceeding 5.0% of total batch weight.
6. Mix 5 minutes (2 minutes) with the prop mixer.
7. Add the Dextrose, USP.
8. Rinse with three (3) portions of Water for Injection, USP/EP total not exceeding 5.0% of total batch weight.
9. Mix for 10 minutes (2 minutes) with the prop mixer or until all Dextrose is dissolved.
10. Add the Safingol.
11. Rinse with three (3) portions of Water for Injection, USP/EP total not exceeding 5.0% of total batch weight.
12. Mix for 30 minutes (5 minutes) with the rotor/stator mixer until all Safingol is dissolved.
13. Add the Lipoid E80®.
14. Rinse with three (3) portions of Water for Injection, USP/EP total not exceeding 5.0% of total batch weight.
15. Mix for 25 minutes (5 minutes) with the rotor/stator mixer or until all Lipoid E80® is dissolved.
16. QS to final batch weight with Water for Injection, USP/EP and adjust vessel temperature to +2° C. to +8° C.
17. Mix solution with rotor/stator mixer for 10 minutes (2 minutes).

B. Microfluidizer Set-Up:
1. Set up Microfluidizer. Record date and time.
2. Clean Microfluidizer thoroughly using between 20 liters to 40 liters of Isopropanol, USP and discard the isopropanol. Operate the Microfluidizer at 5,000 psi during this rinsing procedure. Record the volume of rinse (L) and pressure (psi).
3. Rinse the Microfluidizer using between 30 liters to 50 liters of Water for Injection, USP/EP and discard the water. Operate Microfluidizer at 10,000 psig during rinsing procedure. Flow rate should be approximately 0.84 L/minute. If the flow rate is less than 0.5 L/minute, the interaction chamber will need to be back-flushed prior to proceeding.
4. Set up the cooling water supply for temperatures between +2° C. to +15° C. NOTE: Chilled water will be supplied to the interaction chamber-cooling jacket and the Microfluidizer cooling jacket on the outlet tubing.
5. Connect the cold water lines to the water inlets of the cooling jacket for the interaction chamber and the product-cooling jacket inlets.
6. Blow any remaining Water for Injection, USP/EP used for rinsing from the vessels, hoses, feed pump valves, and homogenizer. To accomplish this, all of the feed valves must be open and the feed pump should be operating at a fast pumping rate for sufficient elimination of rinse water. Be certain to open all feed pump and homogenizer outlet valves, one at a time, in order to eliminate trapped rinse water.

C. Homogenization:
1. Maintain mixing using prop mixer in each homogenization vessel during the homogenization process.
2. Filter the pre-emulsion from compounding vessel #2 through the Gelman Polypure TDC 1 µm filter (previously flushed with Water for Injection, USP/EP) into homogenization vessel #1 (with bottom-located outlet). Discard first liter. Transfer at approximately 10 to 15 psig. Continue to pressurize the filter for 15 minutes±5 minutes after the bulk of the pre-emulsion has passed through to ensure maximum recovery of the pre-emulsion from the filter. Record the time.
3. Prime the feed pump and pump lines of the homogenizing unit with pre-emulsion, opening pump air purge valves so that the pre-emulsion is returned to the vessel from which it was delivered.

4. Initiate the homogenization process. Operate the Microfluidizer at 17,000 psig to 25,000 psig. The recommended operating pressure range is 23,000 to 25,000 psig. Record the time and pressure (psig).
5. Collect emulsion from the outlet of the homogenizer into homogenization vessel #2. At the end of each pass, open the valve for the freshly filled homogenization vessel while closing the outlet valve for the emptied homogenization vessel. Adjust the 3-way valve on the homogenizer outlet line so the emulsion collects in the empty homogenization vessel for the next pass. Sample for QC according to pass log. Do not wait for QC results. Homogenize one pass after QC specification is met. Complete the pass log entries as required.
6. Measure and record post-homogenization pH for historical information. Typical pH range is 3.0 to 4.0 after homogenization. Hold solution at +2° C. to +8° C. if there are extended interruptions in processing.
7. Once acceptable particle size results are obtained, withdraw a 20 mL "Before Filtration, Post-homogenization" sample and deliver to Quality Control wrapped in foil. Wait for QC results.
8. Withdraw and submit 2×20 mL bioburden samples to Environmental Control.
9. Obtain the final weight of the homogenized emulsion.

In Process Analysis:

TABLE 7

IN-PROCESS ANALYSIS AND SPECIFICATIONS

| TEST | METHOD | SPECIFICATION |
|---|---|---|
| Appearance | 999-00-001 | Light yellow, hazy emulsion essentially free from visible contaminants. |
| pH | 999-00-002 | Report for information only; typically 3.0 to 4.0 at 25° C. ± 2° C. |
| Density | 999-00-003 | Between 1.014 g/mL to 1.024 g/mL (target: 1.019 g/mL) at 25° C. ± 2° C. |
| Particle Size | 2112-00-014 | 90% of particles are less than 0.24 μm. |
| Potency (ELSD) | 2112-00-024 | Not less than 1.90 mg/mL and not more than 2.10 mg/mL (95.0% to 105.0% of target concentration). |

TARGET DENSITY: 1.019 g/mL.

EXAMPLE 5

Stability of Safingol Emulsion

BVL Pilot Lot SG042502 was placed on stability (up and inverted) at refrigerated temperature (2° C. to 8° C.). Assay and particle sizes are shown below in Table 8. pH and appearance are shown below in Table 8. Formulation details are as follows:

| | |
|---|---|
| Safingol | 2.0 mg/mL |
| Lactic Acid | 1.2 mg/mL |
| Lipoid e80 ® | 20 mg/mL |
| Dextrose | 45 mg/mL |

TABLE 8

Particle Size Distribution, Assay, and pH Results for Pilot Lot SG042502
2 to 8° C., 2 mg/mL n = 2

| | | MV (μm) | 90% (μm) | HIGH (μm) | LOW (μm) | mg/mL | % |
|---|---|---|---|---|---|---|---|
| Time Zero | | 0.0156 | 0.0250 | 0.1022 | 0.0090 | 2.06 | 103.00 |
| 1 MONTH | UP | 0.0142 | 0.0187 | 0.1022 | 0.0090 | 2.01 | 100.52 |
| | INV | 0.0144 | 0.0187 | 0.1022 | 0.0090 | 1.99 | 99.31 |
| 2 MONTHS | UP | 0.0156 | 0.0225 | 0.1022 | 0.0107 | 1.99 | 99.67 |
| | INV | 0.0158 | 0.0223 | 0.1022 | 0.0107 | 2.02 | 100.91 |
| 3 MONTHS | UP | 0.0156 | 0.0222 | 0.1022 | 0.0090 | 2.01 | 100.65 |
| | INV | 0.0134 | 0.0173 | 0.0859 | 0.0090 | 2.01 | 100.50 | pH and Appearance

TABLE 9

Particle Size Distribution, Assay, and pH Results for Pilot Lot SG042502
2 to 8° C., 2 mg/mL n = 2

| | | pH | Appearance |
|---|---|---|---|
| Time Zero | | 3.73 | Pale yellow, slightly hazy with no visible particulates. |
| 1 MONTH | UP | 3.71 | Pale yellow, slightly hazy with no visible particulates. |
| | INV | 3.70 | Pale yellow, slightly hazy with no visible particulates. |
| 2 MONTHS | UP | 3.78 | Pale yellow, slightly hazy with no visible particulates. |
| | INV | 3.82 | Pale yellow, slightly hazy with no visible particulates. |
| 3 MONTHS | UP | 3.75 | Pale yellow, slightly hazy with no visible particulates. |
| | INV | 3.75 | Pale yellow, slightly hazy with no visible particulates. |

Results demonstrated that the emulsion of the invention was stable for at least 3 months at refrigerator temperatures, making it useful for medicinal purposes.

As shown in Table 10 below, additional studies show that safingol emulsions 100 mg/50 mL/vial (2 mg/mL), were stable for at least 9 months at temperatures from about 2° C. to about 8° C.

TABLE 10

| Test | Requirements | | Initial D1 | Initial D2 | Initial D3 | 3 Months | 6 Months | 9 Months |
|---|---|---|---|---|---|---|---|---|
| Appearance | Light yellow, hazy emulsion | | Meets Req. | Meets Req. | Meets Req. | Meets Req. | Meets Req. | Meets Req. |
| Color | Light yellow | | Meets Req. | N/A | N/A | Meets Req. | Meets Req. | Meets Req. |
| pH | Limit not yet established (typically 3.0 to 4.0) | | 3.76 | N/A | N/A | 3.70 | 3.72 | 3.64 |
| Particle Size Analysis (data from BenVenue) | "Report results" | 90% | 0.0469 0.0421 | N/A | N/A | 0.0267 0.0277 | 0.0303 0.0272 | 0.0263 0.0307 |
| | ≦0.2 microns | Mean | 0.0232 0.0213 | N/A | N/A | 0.0173 0.0176 | 0.0174 0.0169 | 0.0173 0.0175 |
| HPLC Assay (% Label Claim) | 90.0% to 110.0% LC | | 96.4 94.8 Avg of 3: | 95.8 96.6 97.2 | 99.4 100.0 | 94.5 94.2 94.9 94.5 | 105.5 105.1 102.1 104.2 | 98.6 99.9 101.2 99.9 |
| Impurity* % total peak area | For Information Only | RRT 0.88-0.90 | 0.3 | 0.3 | 0.4 | 0.1 | 0.4 | 0.4 |
| Total Impurities % total peak area | For Information Only | | 0.3 | 0.3 | 0.4 | 0.1 | 0.4 | 0.4 |

*Impurities less than 0.1% of the total peak area are not reported.

EXAMPLE 6

Tolerability and Coadministration with Fenretinide

Studies were conducted to show that a safingol emulsion of the present invention was well tolerated when co-infused intravenously with fenretinide. As summarized in Table 11 below, results showed that, overall, only minor liver toxicity was observed. The data indicate that the safingol emulsions of the present invention are tolerated in rats when given intravenously, and therefore, suitable for medicinal use.

TABLE 11

DRF Study of 4-HPR(NCS-374551) + Safingol (NSC-714503) in Rats 9500.15.12

| Group[a] | 4-HPR (mg/kg/d) | 4-HPR mg/m²/d | Schedule (continuous) | safingol (mg/kg/hr) | safingol (mg/m²/d) | Schedule (continuous) | Toxicity |
|---|---|---|---|---|---|---|---|
| I | 0 | 0 | D1-5 | 0 | 0 | D1-2 | clinical signs: normal<br>clin path: normal<br>necropsy: hernia(liver) - 2/3 |
| II | 0 | 0 | D1-5 | 0 | 0 | D1-5 | clinical signs: normal<br>clin path: normal<br>necropsy: discoloration(lung) - 2/3 |
| III | 61 | 366 | D1-5 | 0 | 0 | D1-5 | clinical signs: normal<br>clin path: normal<br>necropsy: discoloration(lung) - 3/3, emaciation - 1/3 |
| IV | 61 | 366 | D1-5 | 0.4 | 24 | D1-5 | clinical signs: normal<br>clin path: ALT 1.3X, ALP 1.7X<br>necropsy: discoloration(lung) - 2/3 |
| V | 61 | 366 | D1-5 | 1 | 6 | D1-2 | clinical signs: moribund sac Day 3 in 1/3 (fluid in pleural cavity)<br>clin path: ALT 1.6X, ALP 1.8X<br>necropsy: discoloration(lung) - 2/3, fluid in pleural cavity - 1/3 |
| VI | 61 | 366 | D1-5 | 1 | 6 | D3-4 | clinical signs: normal<br>clin path: ALT 1.3X, ALP 1.6X<br>necropsy: discoloration(lung) - 3/3 |
| VII | 95 | 570 | D1-5 | 0.4 | 24 | D1-5 | clinical signs: normal<br>clin path: ALT 1.3X, ALP 1.8X<br>necropsy: discoloration(lung) - 1/3 |
| VIII | 95 | 570 | D1-5 | 1 | 6 | D1-2 | clinical signs:<br>clin path: ALT 1.6X, ALP 2X<br>necropsy: |
| IX | 95 | 570 | D1-5 | 1 | 6 | D3-4 | clinical signs: normal<br>clin path: ALT 1.3X, ALP 1.6X<br>necropsy: discoloration(lung&kidney) - 1/3 |

[a] 3 males/group

Safingol emulsion (safingol 2 mg/ml; lactic Acid: 1.2 mg/mL; dextrose 45.4 mg/mL; Lipoid e80® 20 mg/mL) was administered intravenously as a continuous infusion to Fisher rats at the doses and schedule indicated, with or without fenretinide. emulsion (an anti-cancer retinoid). D=Experiment Day.

The foregoing is illustrative of the present invention, and is not to be construed as limiting thereof. The invention is defined by the following claims, with equivalents of the claims to be included therein.

That which is claimed is:

1. A stable aqueous solution consisting essentially of
  (a) a sphingolipid;
  (b) lactic acid; and
  (c) an alcohol or mannitol;
  said solution having a molar ratio of lactic acid to sphingolipid of 1:1 to 10:1.

2. A reconstitutible composition produced by the process of lyophilizing a solution of claim 1.

3. A reconsititutible composition produced by the process of lyophilizing a solution comprising safingol stabilized in lactic acid, wherein a molar ratio of lactic acid to L-threo-dihydrosphinaosine or safingol is about 3.5:1 to about 4:1, safingol is present in an amount of about 2.5 to about 5.0 mg/ml, the solution further comprising ethanol in an amount of about 20 mg/ml or mannitol in an amount of about 5 mg/ml.

4. A method of treating cancer in a subject in need thereof, comprising administering to the subject a treatment effective amount of a solution of claim 1, wherein said cancer is selected from the group consisting of leukemia, lymphoma, neuroblastoma, lung cancer, skin cancer, prostate cancer, colon cancer, breast cancer, ovarian cancer, cervical cancer, brain cancer, and pancreatic cancer.

5. The method of claim 4, wherein the sphingolipid is selected from the group consisting of sphingosine, dihydrosphingosine, D-threo-dihydrosphingosine, L-threo-dihydrosphingosine, DL-threo-dihydrosphingosine, lysosphingolipids, combinations thereof and pharmaceutically acceptable salts thereof.

6. The method of claim 4, wherein the solution is administered orally or parenterally.

7. The method of claim 4, wherein the solution is administered parenterally.

8. The method of claim 4, wherein the solution is administered intravenously.

9. The method of claim 4, wherein the subject is a human or animal subject.

10. An emulsion formulation consisting essentially of:
  (a) lactic acid;
  (b) a sphingolipid, wherein the sphingolipid is present in an amount of about 0.1 to about 30 mg/ml of solution;
  (c) optionally an isotonic agent; and
  (d) a phospholipid present in an amount of about 0.2 to about 200 mg/mi of emulsion.

11. The emulsion of claim 10, wherein the sphingolipid is selected from the group consisting of sphingosine, dihydrosphingosine, D-threo-dihydrosphingosine, L-threo-dihydrosphingosine, DL-threo-dihydrosphingosine, lysosphingolipids, combinations thereof and pharmaceutically acceptable salts thereof.

12. The emulsion of claim 11, wherein the sphingolipid is L-threo-dihydrosphingosine or safingol.

13. The emulsion of claim 10 wherein the aqueous medium is water.

14. The emulsion of claim 10, wherein a molar ratio of lactic acid to sphingolipid is about 1 to about 10:1.

15. The emulsion of claim 10, wherein the isotonic agent is glucose.

16. The emulsion of claim 10, wherein the phospholipid is selected from the group consisting of phosphatidylcholine, phosphatidylethanolamine, pho sphatidylserine, phosphatidylinositol, phosphatidylglycerol, phosphatidic acid, lysophospholipid, egg phospholipid, soybean phospholipid and combinations thereof.

17. The emulsion of claim 10, wherein the mean particle size of the emulsion is less than about 0.03 microns.

18. The emulsion of claim 10, wherein the emulsion has a shelf-life of at least six months at a temperature from about 2° C. to about 8° C.

19. A method of making an emulsion comprising a sphingolipid stabilized in an aqueous medium, comprising:
  (a) dissolving the sphingolipid in a dilute lactic acid solution, wherein the sphingolipid is present in an amount of about 0.1 to about 30 mg/ml of solution;
  (b) optionally adding an isotonic agent; and
  (c) adding a phospholipid to the product resulting from (a) or (b) to thereby form said emulsion.

20. A method of treating cancer in a subject in need thereof, comprising administering to the subject a treatment effective amount of an emulsion of claim 10, wherein said cancer is selected from the group consisting of leukemia, lymphoma, neuroblastoma, lung cancer, skin cancer, prostate cancer, colon cancer, breast cancer, ovarian cancer, cervical cancer, brain cancer, and pancreatic cancer.

21. The method of claim 19, wherein the sphingolipid is selected from the group consisting of sphingosine, dihydrosphingosine, D-threo-dihydrosphingosine, L-threo-dihydrosphingosine, DL-threo-dihydrosphingosine, lysosphingolipids, combinations thereof and pharmaceutically acceptable salts thereof.

22. The method of claim 19, wherein the phospholipid is selected from the group consisting of phosphatidyicholine, phosphatidylethanolamine, phosphatidylserine, phosphatidylinositol, phosphatidylglycerol, phosphatidic acid, lysophospholipid, egg phospholipid, soybean phospholipid and combinations thereof.

23. The method of claim 20, wherein the cancer is selected from the group consisting of leukemia, lymphoma, neuroblastoma, lung cancer, skin cancer, prostate cancer, colon cancer, breast cancer, ovarian cancer, cervical cancer, brain cancer, and pancreatic cancer.

24. The method of claim 20, wherein the emulsion is administered orally or patenterally.

25. The method of claim 20, wherein the emulsion is administered parenterally.

26. The method of claim 20, wherein the emulsion is administered intravenously.

27. The method of claim 20, wherein the subject is a human or animal subject.

* * * * *

UNITED STATES PATENT AND TRADEMARK OFFICE
CERTIFICATE OF CORRECTION

PATENT NO. : 7,476,692 B2  
APPLICATION NO. : 10/782459  
DATED : January 13, 2009  
INVENTOR(S) : Gupta et al.

It is certified that error appears in the above-identified patent and that said Letters Patent is hereby corrected as shown below:

Column 1, Lines 35-40: Please replace with the following structure illustrating correct shading:

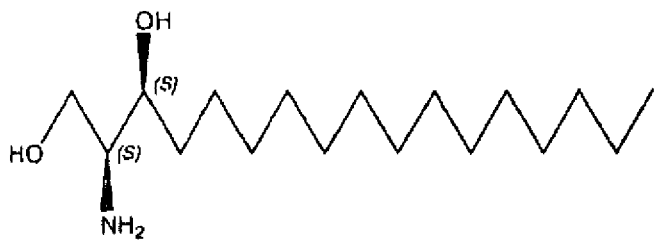

Safingol (L-threo-dihydrosphinganine)

Column 22, Line 13: Please add -- Assay and Particle Size -- before line 14 "Table 8".

Column 23 and 24, Table 10, Lines 13-27: Please correct table alignment as follows:

| Test | Requirements | | Initial D1 | Initial D2 | Initial D3 | 3 Months | 6 Months | 9 Months |
|---|---|---|---|---|---|---|---|---|
| (data from BenVenue) | | | 0.0421 | | | 0.0277 | 0.0272 | 0.0307 |
| | ≤ 0.2 microns | Mean | 0.0232 | N/A | N/A | 0.0173 | 0.0174 | 0.0173 |
| | | | 0.0213 | | | 0.0176 | 0.0169 | 0.0175 |
| HPLC Assay (% Label Claim) | 90.0% to 110.0% LC | | 96.4 | 95.8 | 99.4 | 94.5 | 105.5 | 98.6 |
| | | | 94.8 | 96.6 | 100.0 | 94.2 | 105.1 | 99.9 |
| | | | | | | 94.9 | 102.1 | 101.2 |
| | | Avg of 3: | | 97.2 | | 94.5 | 104.2 | 99.9 |
| Impurity * % total peak area | For Information Only | RRT 0.88-0.90 | 0.3 | 0.3 | 0.4 | 0.1 | 0.4 | 0.4 |
| Total Impurities % total peak area | For Information Only | | 0.3 | 0.3 | 0.4 | 0.1 | 0.4 | 0.4 |

UNITED STATES PATENT AND TRADEMARK OFFICE
CERTIFICATE OF CORRECTION

PATENT NO. : 7,476,692 B2
APPLICATION NO. : 10/782459
DATED : January 13, 2009
INVENTOR(S) : Gupta et al.

It is certified that error appears in the above-identified patent and that said Letters Patent is hereby corrected as shown below:

Column 24, Table 11, Lines I-IX: Please correct "dinical signs" and "din path" to read -- clinical signs -- and -- clin path -- in the "Toxicity" column.

Column 26, Claim 16, Line 11: Please correct "pho sphatidylserine" to read -- phosphatidylserine --.

Column 26, Claim 22, Line 42: Please correct "phosphatidyicholine" to read -- phosphatidylcholine --.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,476,692 B2  Page 1 of 1
APPLICATION NO. : 10/782459
DATED : January 13, 2009
INVENTOR(S) : Gupta et al.

It is certified that error appears in the above-identified patent and that said Letters Patent is hereby corrected as shown below:

On Title Page:
Item 73, Assignee: Please correct to read
-- Childrens Hospital Los Angeles, Los Angeles, CA (US); and The Government of the United States of America, as represented by The Secretary of the Department of Health and Human Services, Rockville, MD (US) --

Signed and Sealed this
Twelfth Day of June, 2012

David J. Kappos
*Director of the United States Patent and Trademark Office*